United States Patent
Grodzins

(12) 
(10) Patent No.: US 6,282,260 B1
(45) Date of Patent: Aug. 28, 2001

(54) UNILATERAL HAND-HELD X-RAY INSPECTION APPARATUS

(75) Inventor: Lee Grodzins, Lexington, MA (US)

(73) Assignee: American Science & Engineering, Inc., Billerica, MA (US)

(*) Notice: Subject to any disclaimer, the term of this patent is extended or adjusted under 35 U.S.C. 154(b) by 0 days.

(21) Appl. No.: 09/458,479

(22) Filed: Dec. 9, 1999

Related U.S. Application Data

(60) Provisional application No. 60/112,102, filed on Dec. 14, 1998, and provisional application No. 60/113,412, filed on Dec. 22, 1998.

(51) Int. Cl.[7] .................................................. G01N 23/201
(52) U.S. Cl. .............................. 378/87; 378/137; 378/88; 378/86
(58) Field of Search .................................... 378/87, 88, 86, 378/102, 83, 98.8, 137; 250/498.1

(56) References Cited

U.S. PATENT DOCUMENTS

| | | | |
|---|---|---|---|
| 4,267,446 | 5/1981 | Brown et al. ........................ | 250/255 |
| 5,068,883 | * 11/1991 | DeHaan et al. . | |
| 5,077,771 | * 12/1991 | Skillicorn et al. . | |
| 5,181,234 | * 1/1993 | Smith . | |
| 5,692,029 | 11/1997 | Husseiny et al. ...................... | 378/88 |
| 5,696,806 | 12/1997 | Grodzins et al. ...................... | 378/86 |
| 5,763,886 | 6/1998 | Schulte .............................. | 250/358.1 |

FOREIGN PATENT DOCUMENTS

WO 97/01089   1/1997   (WO).

* cited by examiner

*Primary Examiner*—David P. Porta
*Assistant Examiner*—Pamela R. Hobden
(74) *Attorney, Agent, or Firm*—Bromberg & Sunstein LLP

(57) ABSTRACT

A hand holdable inspection device for three-dimensional inspection of a volume distal to a surface. The inspection device has a hand-holdable unit including a source of penetrating radiation for providing a beam of specified cross-section and a detector arrangement for detecting penetrating radiation from the beam scattered by the object in the direction of the detector arrangement and for generating a scattered radiation signal. Additionally, the inspection device has a controller for characterizing the volume based at least on the scattered radiation signal. The detector arrangement includes one or more backscatter detectors that may be disposed asymmetrically with respect to the beam and at differing displacements with respect to the surface.

18 Claims, 7 Drawing Sheets

UNILATERAL HAND-HELD X-RAY INSPECTION APPARATUS

The present application claims priority from U.S. Provisional Application No. 60/112,102, entitled "Unilateral Hand-Held X-Ray Inspection Apparatus," filed Dec. 14, 1998, and from U.S. Provisional Application No. 60/113,412, entitled "Separate Lateral Processing of Backscatter Signals," filed Dec. 22, 1998, both of which applications are incorporated herein by reference.

TECHNICAL FIELD

The present invention relates to an apparatus for imaging a concealed target by unilateral irradiation and detection of penetrating radiation.

BACKGROUND OF THE INVENTION

Schulte (U.S. Pat. No. 5,763,886) teaches a two-dimensional imaging backscatter probe for using a source of gamma-rays to illuminate a surface and for generating a two-dimensional image of the backscattered radiation. It is valuable, in many applications, to know the shape and volumetric distribution as well as material characteristics of objects lying behind or beneath the illuminated surface. Schulte, however, fails to suggest that any depth or compositional information may be obtained with respect to objects lying behind or beneath the illuminated surface or to teach any manner in which such information may be obtained. Additionally, Schulte requires that the probe be moved and that the position of the radiation detectors with respect to the target be sensed using means external to the probe in order to map the backscattered radiation.

SUMMARY OF THE INVENTION

In accordance with one aspect of the invention, in one of its embodiments, there is provided a hand-holdable inspection device for three-dimensional inspection of a volume distal to a surface. The inspection device has a hand-holdable unit including a source of penetrating radiation for providing a beam of specified cross-section and a detector arrangement for detecting penetrating radiation from the beam scattered by the object in the direction of the detector arrangement and for generating a scattered radiation signal. Additionally, the inspection device has a controller for characterizing the volume based at least on the scattered radiation signal.

In accordance with alternate embodiments of the invention, the source of penetrating radiation may be an x-ray source, the source may include a scanner, such as an electronic scanner, for scanning a direction of emission of the beam, the detector arrangement may be integral to the hand-holdable unit and may include an array of semiconductor detectors, and the inspection device may additionally have a display screen for displaying an image characterizing the volume distal to the surface.

BRIEF DESCRIPTION OF THE DRAWINGS

The foregoing features of the invention will be more readily understood by reference to the following detailed description taken with the accompanying drawings.

DETAILED DESCRIPTION OF THE PREFERRED EMBODIMENTS

Figure 1:
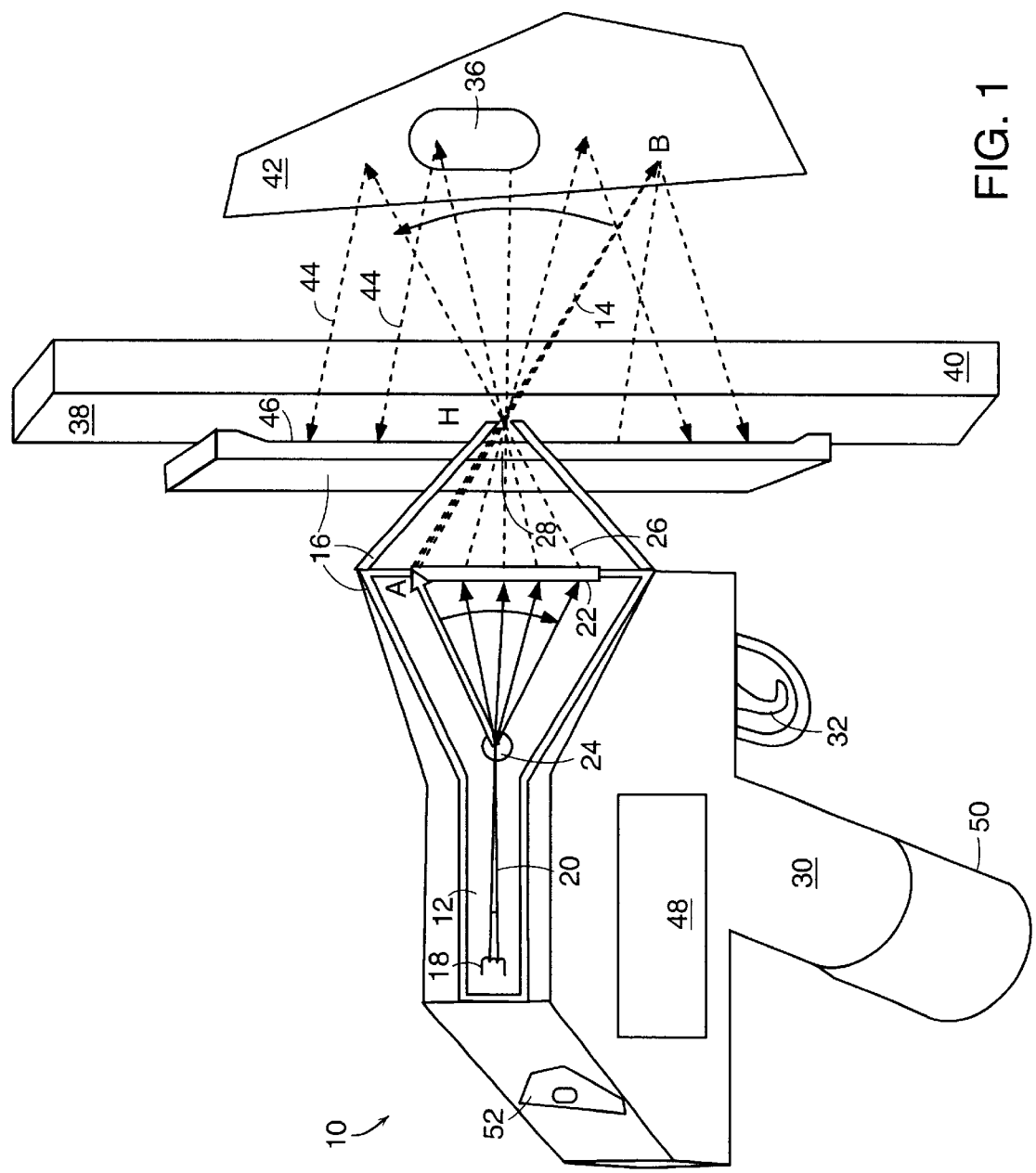
FIG. 1 provides a side view of an inspection system employing a hand-held source, detector, and display of penetrating radiation in accordance with a preferred embodiment of the present invention.

FIG. 1 shows a side view of the elements of an x-ray inspection device, designated generally by numeral 10. A source 12 emits penetrating radiation in a beam 14. Beam 14 of penetrating radiation, may be, for example, a beam of x-rays such as a polychromatic x-ray beam. The cross-sectional shape of beam 14 may be determined by the geometry of source 12 and a collimating arrangement such as an aperture 28 provided in shielding 16. Source 12 of penetrating radiation is preferably an cathode ray tube x-ray generator with a sweeping electron beam, as shown. Electron gun 18 emits an electron beam 20 that is accelerated toward anode 22 by virtue of the large positive electrical potential applied to anode 22 with respect to electron gun 18 as well known in the art of x-ray generation. Since electrons comprising electron beam 20 bear electrical charge, their path may be modified by electrical or magnetic deflector means well known in the art. A deflector (otherwise referred to herein also as a "steerer") 24 employing one or both of electrical or magnetic deflector means is disposed along the path of electron beam 20 between electron gun 18 and anode 20. By application of an electrical potential or magnetic field to deflector 24, electron beam 20 may be scanned across anode 22 in a controlled manner such as a raster scanning pattern. X-rays are generated as electron beam 20 impinges upon anode 20. The emitted x-rays 26 are coupled through aperture 28 in shielding 16 such that, as electron beam 20 is scanned across anode 22, the orientation of the emergent x-ray beam 14 is swept correspondingly. A high-voltage potential and electron beam control potentials may be derived using on-board power supplies and a local battery 50.

X-ray inspection device 10 may readily be held by an operator who can grip handle 30 and activate the emission of x-ray beam 14 by operation of trigger 32. The x-ray inspection device is advantageously employed for detecting the presence of an object 36 or cavity or other anomaly in a region posterior to the front surface 38 of a wall 40, under circumstances where only front surface 38 is accessible to the operator. Inspection of the surface and of the volume disposed distally to the surface may thus be accomplished with only unilateral access to wall 40. Additionally, object 36 may be imaged, as described below.

X-rays 14 impinging on object 36 and on surrounding medium 42 are scattered by the respective matter through the process of Compton scattering. Backscattered radiation is designated by dashed rays labeled 44. Scattered radiation is detected by one or more backscatter detectors (not shown) which constitute detector arrangement 46 disposed on device 10 on the side of shielding 16 facing outward from the device and toward the object or surface undergoing inspection. In a preferred embodiment of the invention, detector arrangement 46 is an array of x-ray detectors arranged in a planar configuration. Within the scope of the invention, any x-ray detection technology known in the art may be employed for scatter detector arrangement 46. The detectors may be segmented scintillators or other solid state detectors, for example, or photomultipliers or liquid scintillators which may be doped with tin or other metal. The use of cesium-iodine on PIN diodes and of room-temperature CdZnTe semiconductors are examples of detector technologies which may be employed. Energy resolution of detector arrangement 46 is within the scope of the present invention and advantageously allows a determination of material characteristics of the object according to algorithms well-known in the art.

Output signals from the scatter detectors are transmitted to a processor 48, and processed to obtain images of object 36 and its surrounding medium 42, or to obtain other characteristics such, for example, as mass, mass density, mass distribution, mean atomic number, or likelihood of containing targeted threat material, all as known to persons skilled in the art of x-ray inspection. The distribution of detected radiation as beam 14 is swept in orientation allows a two-dimensional image of the concealed volume to be obtained. The term "image" refers to a mapping of raw or processed detector signals to positions in the plane, and may be stored in an internal or external memory, or, alternatively, may be displayed visually on a display 52 such as a video monitor.

Figure 2:
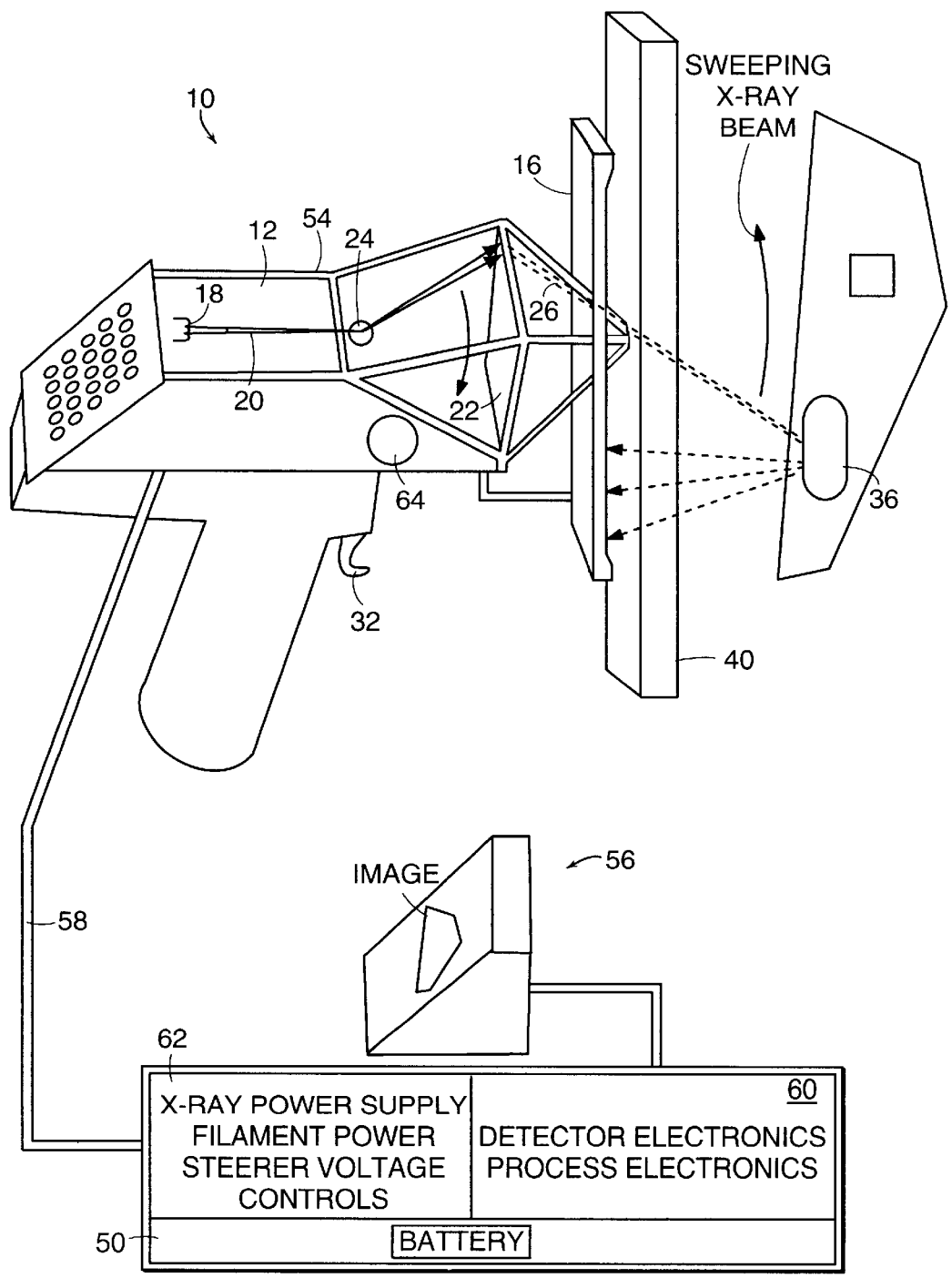
FIG. 2 is a side view of an inspection system employing a hand-held source and detector assembly, with an external display and control unit in accordance with an embodiment of the present invention.

Referring now to FIG. 2, portions of x-ray inspection system 10 may be separated from hand-held unit 54 and may be included in base unit 56 connected to hand-held unit 54 via cable 58 or via any other appropriate means of communication with hand-held unit 54. Base unit 56 may contain, for example, a controller 60 for processing the signals provided by detector assembly 16 and/or battery supply 50 and power conditioning electronics 62 to provide power for electron gun filament 18 of source 12 and the electrical potentials applied to control steerer 24 and anode 22. Additionally, base unit 56 may contain display 52 for displaying an image of target 36 posterior to wall 40. An ambient radiation monitor 64 may be provided, in accordance with a preferred embodiment of the invention, so that x-ray beam intensity may be regulated to provide for safe operation of the unit. The use of ambient radiation monitors in the context of x-ray inspection equipment is described in detail in a co-pending U.S. patent application filed Dec. 1, 1998.

Figure 3A:
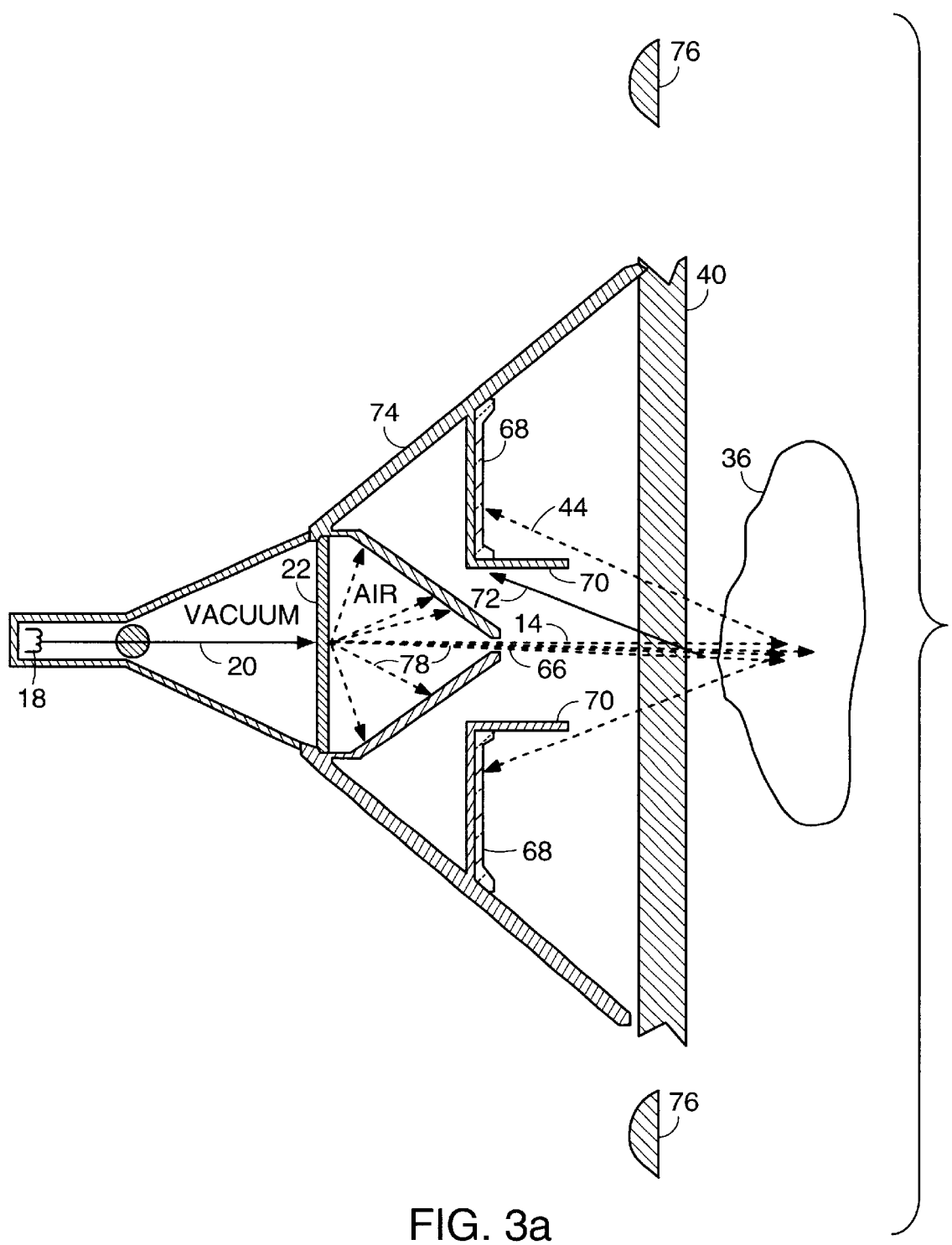
FIG. 3a is a cross-sectional view of the inspection system of FIG. 1, employed in a "Probe" mode, in accordance with an embodiment of the present invention.
Figure 3B:
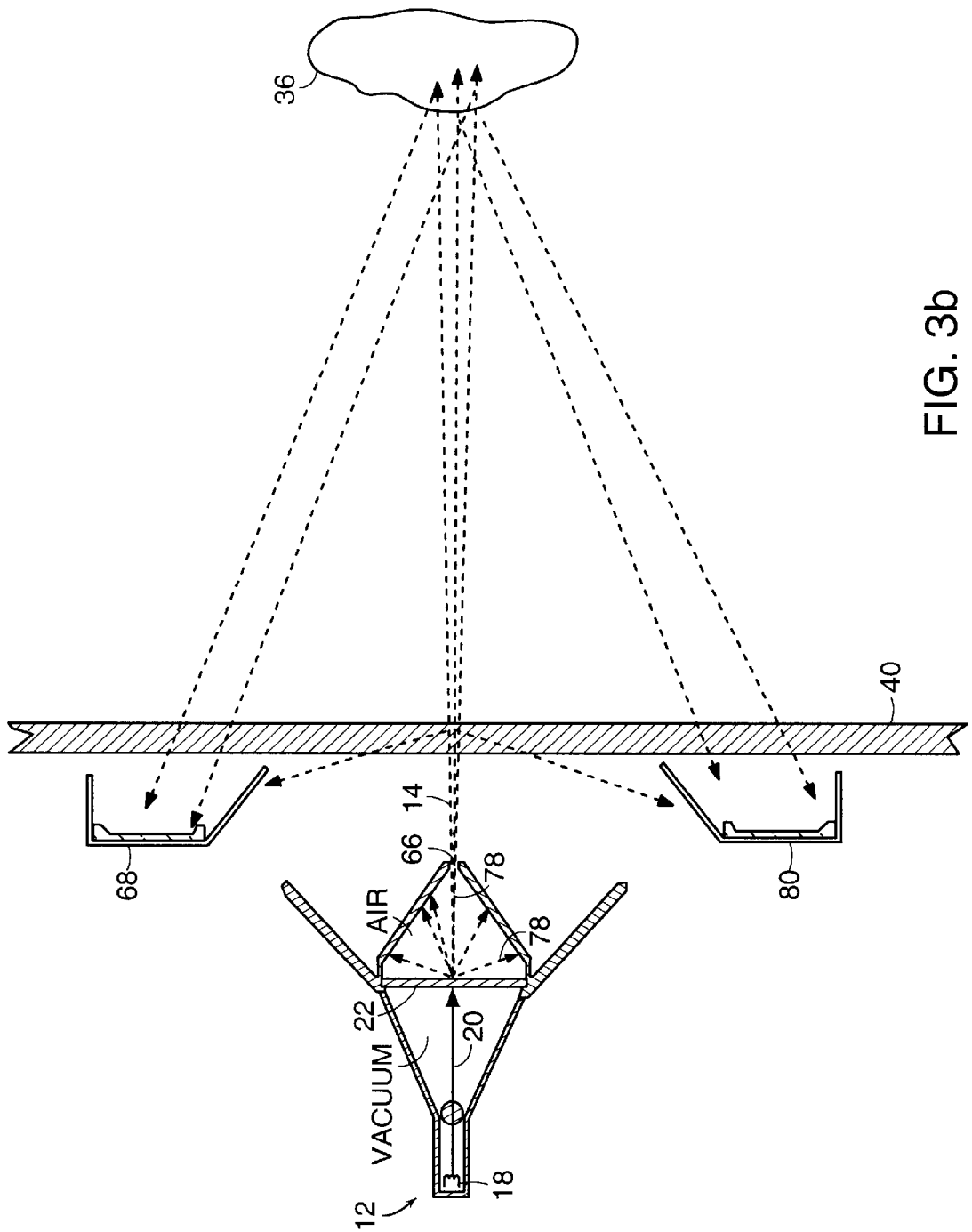
FIG. 3b is a cross-sectional view of a further embodiment of an inspection system, employed in a "Probe" mode, wherein extended backscatter detectors are employed.

Various modes of operation of x-ray inspection system 10 are described with reference to FIGS. 3a–b and 4, wherein like numerals designate identical or similar structural elements of the system. More particularly, operation in a "Probe" mode is described first with reference to FIG. 3a. In the Probe mode, electron beam 20 is maintained in a substantially fixed orientation relative to anode 22 such that, from among x-rays 78 generated at anode 22, x-ray beam 14 is emitted through beam forming snout 66 in a substantially forward direction toward, and incident normally upon, wall 40. Scattered x-ray radiation 44 from object 36 is detected by backscatter detectors 68. Shielding 70 may be provided to discriminate against radiation 72 scattered by any source near to the inspection apparatus, such as in the wall facing itself. Further shielding 74 may be provided to protect personnel from scattered radiation.

Any method of determining the absolute or relative position in space of hand-held unit 10 in order to infer the position behind wall 40 of target 36 is within the scope of the present invention. As examples, and without limitation, optical or other electromagnetic locators 76, or acoustic locators, may be employed to allow mapping via triangulation of the position of unit 10 and thereby to image and/or display backscatter signals vs. position.

In accordance with another embodiment of "Probe" mode operation, backscatter detectors 68 and 80 may be displaced in a direction either tangential to or perpendicular to wall 40, either symmetrically with respect to beam 14 or asymmetrically. By separately processing the backscatter signals derived respectively at distinct laterally displaced backscatter detectors, the depth of object 36 may be determined in accordance with the detailed teachings of copending U.S. Provisional Patent Application 60/113,412, filed Dec. 22, 1998, and entitled "Separate Lateral Processing of Backscatter Signals."

Figure 4A:
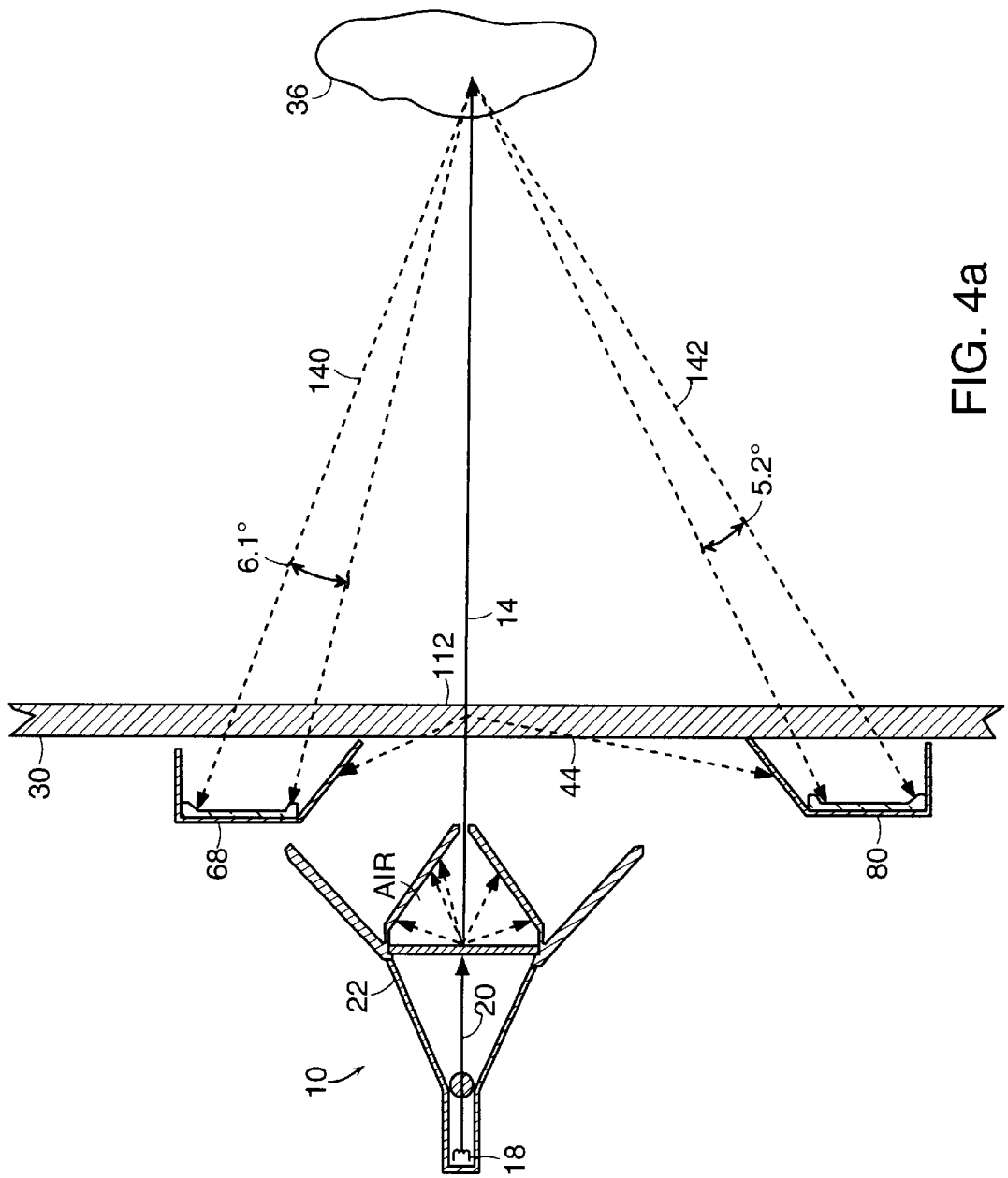
FIG. 4a provides a schematic representation of an x-ray system employing backscatter detectors asymmetrically disposed with respect to an illuminating beam in accordance with a preferred embodiment of the present invention.

Referring now to FIG. 4a, the position and relative sizes of backscatter detectors 68 and 80 may be chosen, in accordance with preferred embodiments of the invention, to optimize the efficiency of the system in discriminating among x-rays scattered from various selected regions of the space penetrated by beam 14, and to obtain images that enhance scattering features located at different depths behind wall 30. Comparison of the scattered radiation flux detected at detectors 68 and 80 disposed with lateral asymmetry with respect to beam 14 may advantageously provide a quantitative measure of the distance from the plane of the detectors to scattering object 36 making reasonable assumptions regarding the isotropy of any medium ambient to object 36 through which scattered radiation 140 and 142 propagates to the respective detectors. Scattered radiation 144 scattered from a nearby scattering source 112 may be shielded from detection by one or more of the backscatter detectors 68 and 80.

As shown in FIG. 4a, backscatter detectors 68 and 80 are disposed asymmetrically with respect to beam 14. Detector 68 subtends an angle, in the plane shown, of 6.1° with respect to object 36, whereas detector 80 subtends an angle, in the plane shown, of 5.2° with respect to object 36. The further detector 80 gets a fraction less than 1 of the counts recorded by near counter 3. The ratio of counts detected by the respective counters approaches unity as the distance to object 36 increases (as measured with respect to the separation between detectors 68 and 80). In this discussion, it is assumed, for simplicity, that propagation effects with respect to scattered beams 140 and 142 may be neglected. Knowledge of the orientation of beam 14 may allow the location of object 36 to be derived using straightforward algorithms.

An embodiment of source 10 of beam 14 of penetrating radiation is shown. Beam 20 of electrons emitted by cathode 18 is accelerated toward anode 22. Electron beam 20 may be scanned with respect to anode 22 such that the orientation of beam 14 may be varied.

Figure 4B:
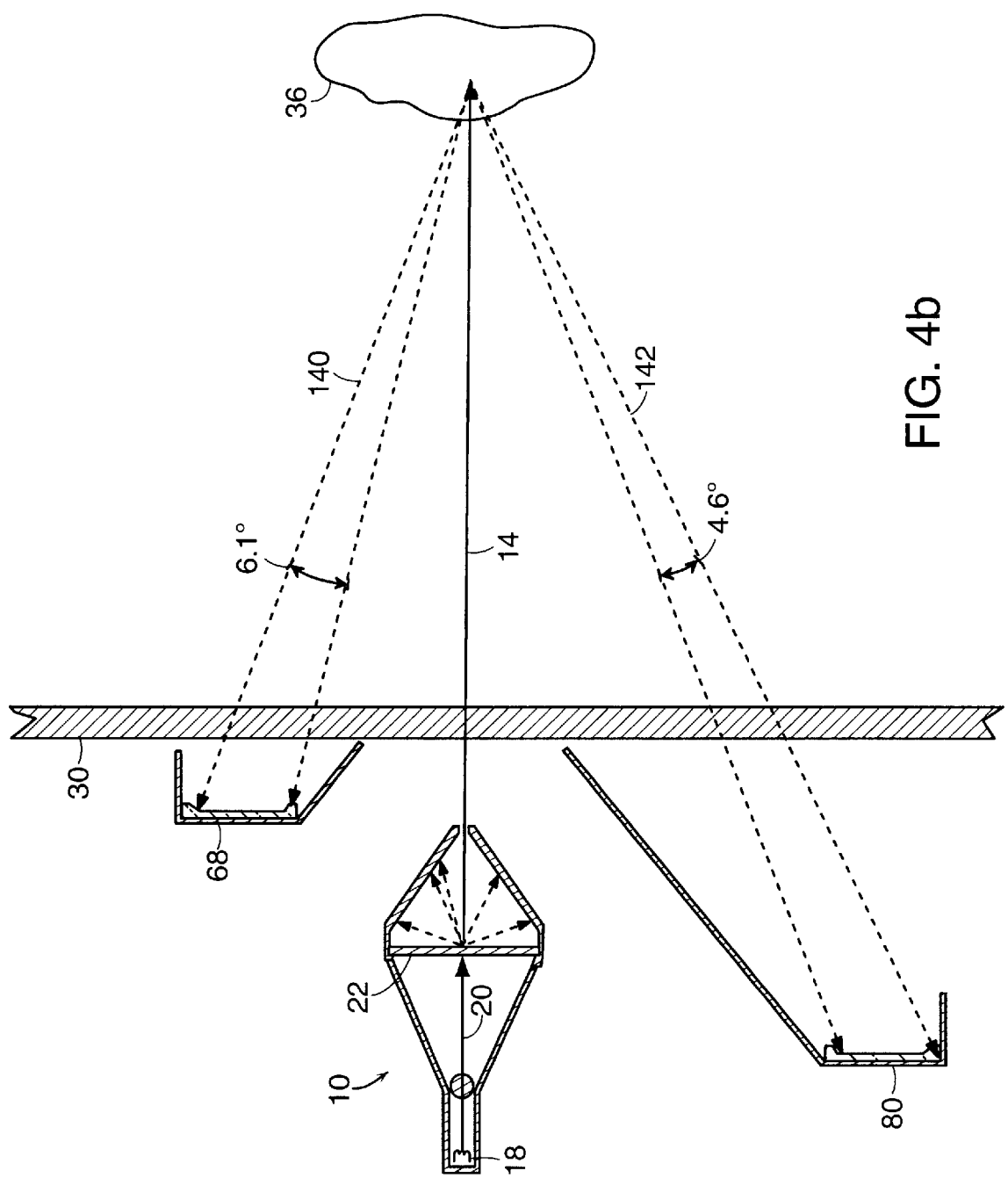
FIG. 4b provides a schematic representation of an x-ray system employing backscatter detectors asymmetrically disposed with respect to an illuminating beam in accordance with a further embodiment of the present invention.

Referring now to FIG. 4b, an alternate embodiment of the invention is depicted in which backscatter detectors 68 and 80 are disposed at different distances with respect to concealing surface 30. As discussed with reference to FIG. 4a, the difference in counts received by detectors 68 and 80 may be used to determine the distance between concealing surface 30 and scattering object 36. Again, the ratio of scatter flux detected by the respective detectors approaches unity as the distance to scattering object 36 increases.

Figure 5:
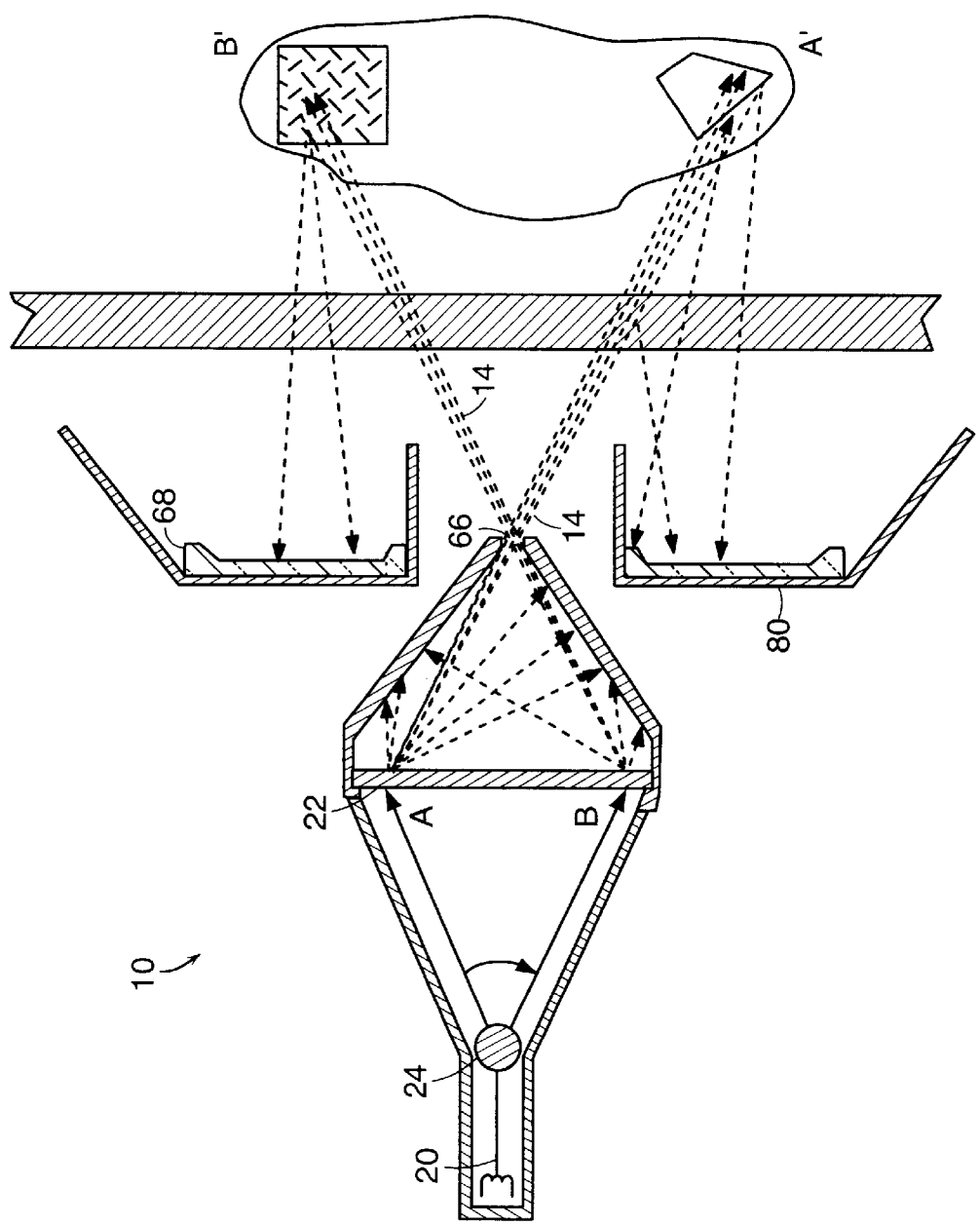
FIG. 5 is a cross-sectional view of an embodiment of an inspection system, employed in an "Image" mode, wherein the direction of the incident x-ray beam is scanned with respect to a detector arrangement fixed with respect to a beam-forming snout associated with the x-ray source.

FIG. 5 depicts operation of x-ray inspection device 10 in an "Image" mode. In this mode, electron beam 20 is swept by deflector 24 across anode 22, such as between positions A and B, indicated for illustrative purposes only. The resultant x-ray beam 14 emitted through beam forming snout 66 is thus scanned as well, impinging at different time intervals on object A' and object B'. Since the orientation of the beam 14 is known at each instant, a map may be derived of the orientation of scattering objects A' and B'. Additionally, since multiple backscatter detectors 68 and 80 are employed, tomographic information may also be derived and the position in space of the scattering objects may be inferred and displayed.

The described embodiments of the invention are intended to be merely exemplary and numerous variations and modifications will be apparent to those skilled in the art. All such variations and modifications are intended to be within the scope of the present invention as defined in the appended claims.

I claim:

1. An inspection device for three-dimensional inspection of a volume distal to a surface, the device comprising:
   a. a hand-holdable unit including a source of penetrating radiation for providing a beam of specified cross-section;
   b. a detector arrangement for detecting penetrating radiation from the beam scattered by the object in the direction of the detector arrangement and for generating a scattered radiation signal; and
   c. a controller for three-dimensional characterization of the volume based at least on the scattered radiation signal such that three-dimensional characterization is performed without motion of the hand-holdable unit.

2. An inspection device according to claim 1, further comprising:
   d. a display screen for displaying an image characterizing the volume distal to the surface.

3. An inspection device according to claim 1, wherein the detector arrangement is integral to the hand-holdable unit.

4. An inspection device according to claim 2, wherein the display screen is integral to the hand-holdable unit.

5. An inspection device according to claim 1, further comprising an electromagnetic locator.

6. An inspection device according to claim 1, further comprising an acoustic locator.

7. An inspection device according to claim 1, wherein the source of penetrating radiation includes a scanner for scanning a direction of emission of the beam.

8. An inspection device according to claim 1, wherein the source of penetrating radiation includes an electronic scanner for scanning a direction of emission of the beam.

9. An inspection system as set forth in claim 1, wherein the source of penetrating radiation is an x-ray source.

10. An inspection system as set forth in claim 1, wherein the detector arrangement includes an array of semiconductor detectors.

11. An inspection system as set forth in claim 1, wherein the detector arrangement includes at least two detectors asymmetrically disposed with respect to the beam.

12. An inspection system as set forth in claim 1, wherein the detector arrangement includes a first scatter detector disposed at a first displacement from the surface and a second detector disposed at a second displacement from the surface.

13. An inspection system as set forth in claim 12, wherein the first displacement is unequal to the second displacement.

14. A method for inspecting a volume distal to a surface, the method comprising:
   a. illuminating the surface with penetrating radiation formed into a beam emitted by a hand-held unit;
   b. detecting penetrating radiation scattered from the volume with a detector arrangement, the detector arrangement including at least two detectors asymmetrically disposed with respect to the beam; and
   c. determining at least one characteristic of the volume based at least on the radiation scattered from the volume.

15. A method according to claim 14, further including the step of varying the orientation of the beam with respect to the surface.

16. A method according to claim 15, further including the step of displaying an image of the volume distal to the surface.

17. An inspection device for inspection of a volume distal to a surface, the device comprising:
   a. a hand-holdable unit including a source of penetrating radiation for providing a beam of specified cross-section;
   b. a detector arrangement for detecting penetrating radiation from the beam scattered by the object in the direction of the detector arrangement and for generating a scattered radiation signal, wherein the detector arrangement includes at least two detectors asymmetrically disposed with respect to the beam; and
   c. a controller for characterization of the volume based at least on the scattered radiation signal such that characterization is performed without motion of the hand-holdable unit.

18. A method for inspecting a volume distal to a surface, the method comprising:
   a. illuminating the surface with penetrating radiation formed into a beam emitted by a hand-held unit;
   b. detecting penetrating radiation scattered from the volume with a detector arrangement; and
   c. performing a three-dimensional characterization of at least one characteristic of the volume based at least on the radiation scattered from the volume.

* * * * *